United States Patent
Schmidt et al.

(10) Patent No.: US 7,045,671 B2
(45) Date of Patent: *May 16, 2006

(54) PROCESS FOR CATALYTIC DEHYDROGENATION AND CATALYST THEREFOR

(75) Inventors: Iver Schmidt, Copenhagen (DK); Anne Krogh, Vedbæk (DK); Claus Hviid Christensen, Copenhagen (DK)

(73) Assignee: Haldor Topsoe A/S, Lyngby (DK)

( * ) Notice: Subject to any disclaimer, the term of this patent is extended or adjusted under 35 U.S.C. 154(b) by 172 days.

This patent is subject to a terminal disclaimer.

(21) Appl. No.: 10/717,484

(22) Filed: Nov. 21, 2003

(65) Prior Publication Data

US 2004/0110630 A1    Jun. 10, 2004

(30) Foreign Application Priority Data

Dec. 10, 2002   (DK) ................................ 2002 01891

(51) Int. Cl.
*B01J 29/06* (2006.01)

(52) U.S. Cl. ................ 585/627; 585/629; 585/630; 585/654; 585/661; 585/662; 502/60; 502/64; 502/66; 502/71; 502/77

(58) Field of Classification Search .................. 502/60, 502/64, 66, 71, 77; 585/616, 627, 629, 630, 585/654, 661, 662
See application file for complete search history.

(56) References Cited

U.S. PATENT DOCUMENTS

| | | | |
|---|---|---|---|
| 5,990,039 A * | 11/1999 | Paul et al. ................... 502/326 |
| 6,087,513 A * | 7/2000 | Liao et al. ................... 549/524 |
| 6,241,960 B1 | 6/2001 | Topsoe et al. |
| 6,287,645 B1 * | 9/2001 | Balkus et al. ................ 427/597 |
| 6,417,135 B1 | 7/2002 | Dyroff |
| 6,565,826 B1 | 5/2003 | Jacobsen et al. |
| 6,620,402 B1 * | 9/2003 | Jacobsen et al. ............. 423/716 |
| 6,887,814 B1 * | 5/2005 | Herbst et al. ................. 502/64 |
| 2002/0034471 A1 | 3/2002 | Jacobsen et al. |
| 2002/0183577 A1 * | 12/2002 | Haw et al. ................... 585/639 |
| 2003/0008770 A1 * | 1/2003 | Srinivas et al. ............. 502/124 |

FOREIGN PATENT DOCUMENTS

| | | |
|---|---|---|
| DE | 100 18 724 A1 | 10/2001 |
| EP | 0 403 462 | 12/1990 |
| EP | 1 106 575 | 6/2001 |
| EP | 1 331 032 | 7/2003 |

OTHER PUBLICATIONS

C. J. Jacobsen et al., "Mesoporous Zeolite 1-12 Single Crystals", *Journal of the American Chemical Society*, vol. 122, No. 29, Jul. 2000, pp. 7116-7117.

A. Dyer, "An Introduction to Zeolite Molecular Sieves." Department of Chemistry and Applied Chemistry, University of Salford, John Wiley & Sons, Chilchester, UK (1988), pp. 1-3.

* cited by examiner

*Primary Examiner*—Christina Johnson
(74) *Attorney, Agent, or Firm*—Dickstein Shapiro Morin & Oshinsky LLP

(57) ABSTRACT

A process for catalytic dehydrogenation of a dehydrogenatable hydrocarbon process stream to the corresponding olefin or olefins, the process comprising contacting the dehydrogenatable hydrocarbon process stream under dehydrogenation conditions with a mesoporous zeotype catalyst having an intra-crystalline, non-crystallographic mesopore system and a mesopore volume of the zeotype crystals above 0.25 ml/g and comprising at least one element belonging to Groups 5–14 in the Periodic Table of the Elements (new notation). The invention also comprises a catalyst for use in the above process.

12 Claims, No Drawings

PROCESS FOR CATALYTIC DEHYDROGENATION AND CATALYST THEREFOR

The invention concerns a catalytic process for dehydrogenating a hydrocarbon process stream containing dehydrogenatable compounds to the corresponding olefins. In particular, the invention concerns the catalytic dehydrogenation of the hydrocarbon process stream using a mesoporous catalyst.

BACKGROUND OF THE INVENTION

Dehydrogenation processes can generally be described as either oxidative or non-oxidative. Oxidative dehydrogenation suffers from the disadvantage of being a highly exothermic reaction. There is also the potential risk of obtaining explosive mixtures of the hydrocarbon feedstock and the di-oxygen containing feed. Operating such a process with a large excess of one of the feed streams does not exclude the possibility of explosive mixtures in local environments.

DE patent application no. 10018724 discloses an oxidative dehydrogenation process using mesoporous materials of the M41S type.

Non-oxidative processes where direct dehydrogenation takes place often suffer from the requirements of frequent catalyst regeneration and associated low carbon yields with respect to the desired olefin-containing products.

Olefins are important raw materials for a wide range of major petrochemical processes. Olefins can be supplied by thermal cracking processes. However, production of olefins by selective dehydrogenation of the corresponding alkanes are often used to meet local demands and/or raw material characteristics.

The invention provides a non-oxidative process whereby the above disadvantages of conventional oxidative and non-oxidative processes are avoided. High yields of olefin-containing products are obtained.

SUMMARY OF THE INVENTION

The invention provides a process for catalytic dehydrogenation of a dehydrogenatable hydrocarbon process stream to the corresponding olefin or olefins, the process comprising contacting the dehydrogenatable hydrocarbon process stream under dehydrogenation conditions with a mesoporous zeotype catalyst having an intra-crystalline, non-crystallographic mesopore system and a mesopore volume of the zeotype crystals above 0.25 ml/g and comprising at least one element belonging to Groups 5–14 in the Periodic Table of the Elements (new notation).

The invention also provides a catalyst for use in the above process wherein the catalyst comprises a mesoporous zeotype catalyst having an intra-crystalline, non-crystallographic mesopore system and a mesopore volume of the zeotype crystals above 0.25 ml/g and comprising at least one element belonging to Groups 5–14 in the Periodic Table of the Elements (new notation).

DETAILED DESCRIPTION OF THE INVENTION

The process of the invention is a catalytic process for selective dehydrogenation of a hydrocarbon process stream containing hydrocarbon compounds that are dehydrogenatable. Hydrocarbon compounds containing a —CH—CH— group are converted to the corresponding —C=C— group without addition of oxidants.

An embodiment of the invention comprises the process whereby the dehydrogenatable hydrocarbon process stream contains one or more dehydrogenatable compounds belonging to the group R—$CH_2$—$CH_3$, where R=H or $C_{1-4}$.

A preferred embodiment of the invention comprises the process, whereby the dehydrogenatable compound is ethane, propane, n-butane or i-butane.

Another embodiment of the invention is the process whereby the dehydrogenatable process stream contains a monocyclic aromatic compound.

A further preferred embodiment of the invention is the process, whereby the monocyclic aromatic compound is ethyl benzene or para-ethyl methylbenzene.

The catalyst comprises a mesoporous zeotype component that is characterised by the features described in U.S. Patent Application No. 2002-0034471 and U.S. Pat. No. 6,565,826, both of which are incorporated herein by reference. Zeotypes as used herein are defined by A. Dyer (An Introduction to Zeolite Molecular Sieves, J. Wiley and Sons, Chichester, 1988).

The catalyst comprises further of one or more elements from Groups 5 to 14 in the Periodic Table of the Elements (new notation). Elements that are especially relevant for the process of the invention are chromium (Cr), Molybdenum (Mo), Wolfram (W), Rhenium (Re), Rhodium (Rh), Iridium (Ir), Nickel (Ni), Palladium (Pd), Platinum (Pt), Copper (Cu), Silver (Ag), Zinc (Zn), Gallium (Ga), Indium (In) and Tin (Sn) in their metal form or as oxides, carbides or nitrides.

A preferred embodiment of the invention is the mesoporous zeotype catalyst comprising the element Rhenium.

U.S. Patent Application No. 2002-0034471 and U.S. Pat. No. 6,565,826 mentioned earlier disclose the preparation of large zeotype primary crystals possessing determined and tunable intra-crystalline mesopore systems, tortuous or straight, respectively. These zeotypes can for instance be mesoporous zeolites such as mesoporous ZSM-5 or mesoporous HZSM-5. They are referred to as mesoporous zeolites.

ZSM-5 crystals prepared according to these disclosures have sizes typically exceeding 0.5 micrometer in two directions as measured by transmission or scanning electron microscopy (TEM or SEM respectively). They have an external surface area greater than 30 $m^2/g$. Although mesoporous ZSM-5 is normally synthesised as an aluminosilicate, the framework aluminium can be partially or completely replaced by other trivalent elements, such as boron, iron and/or gallium or left out completely. The framework silicon can be replaced by other tetravalent elements such as germanium or titanium.

The terms mesoporous and mesopore(s) as used herein refers to mesoporous zeolites containing pores within each individual crystal having a pore size range according to the IUPAC definition of mesopores, i.e. a pore diameter in the range 2–50 nanometer. The catalyst applied in the invention is a solid, crystalline material with the characteristic feature of possessing an intracrystalline mesopore system as well as micropores, where the former is non-crystallographic and the latter is crystallographic. These mesoporous zeolites have at least one XRPD reflection in the 2θ range 8–30 degrees determined by the zeolite type.

The obtained catalyst or catalyst precursor is introduced to a reactor either pure or as a mixture with binder material, inert material or other materials not affecting the catalytic reaction. These materials can be added in order to obtain the desired shape, heat and mass-transfer characteristics and mechanical resistance. Zeolite-based catalysts are these often prepared using suitable binders and/or fillers such as alumina, aluminasilicates, etc.

After activation of the catalyst, a process stream containing the dehydrogenable hydrocarbon compound/reactant is fed through the reactor at reaction temperatures not higher than 800° C. and pressures between 0.1 and 30 bars.

Co-feeding of an alkaline gaseous compound or a compound, which decomposes into an alkaline gaseous compound at the process conditions, modifies the acid characteristics of the catalyst. This enhances the olefin selectivity and lowers the deactivation rate due to coking. The dehydrogenation activity may be optimised by the use of, for instance two elements instead of a single element. Depending on their nature, these two elements may form alloys at the activation and/or process conditions.

Different mesoporous zeotypes, i.e. mesoporous zeolites or mesoporous ALPO4's can be used as components in the desired selective dehydrogenation catalysts in combination with one or more of the dehydrogenating elements mentioned above. In catalytic dehydrogenation processes formation of carbonaceous species, i.e. coke is an inherent problem, which affects the process economy by lowering the yield of desired products as well as lowering the activity of the catalyst. This is circumvented by frequent regeneration of the catalyst by oxidation of the coke in di-oxygen containing gas streams. Thus, a catalyst with increased selectivity towards the primary products, i.e. the corresponding olefins, is highly desirable.

Using the mesoporous catalysts in combination with a dehydrogenation functionality significantly improves the olefin selectivity as well as enables significantly reduced deactivation rates compared to similar catalyst systems based on conventional or non-mesoporous zeotypes. In turn, the enhanced stability with respect to activity allows operational optimisation of the industrial process units.

EXAMPLES

Example 1

Preparation of Mesoporous ZSM-5 Using Carbon Black 2.1 g of NaAlO$_2$ (54 wt % Al$_2$O$_3$, 41 wt % Na$_2$O) is dissolved in a mixture of 172.0 g of tetrapropylammoniumhydroxide solution (TPAOH, 40 wt % aqueous solution) and 25.8 g of distilled water. 151.5 g of ethanol (EtOH, 99% pure) is added and the mixture is impregnated onto 100 g of carbon (Black Pearls BP2000, Cabot Corp., pearl diameter 18 nm), which has previously been dried at 140° C. for 24 hours. The impregnated carbon is left 24 hours at room temperature, whereupon the ethanol evaporates. 193.5 g of tetraethylorthosilicate (TEOS) is impregnated onto the carbon, which is left 24 hours at room temperature. During this period the alkoxides present are hydrolysed. The impregnated carbon is hydrothermally treated in an autoclave, which has been charged with sufficient water to create a saturated steam atmosphere at the hydrothermal crystallisation conditions. The autoclave is heated to 180° C. and held at this temperature for 72 hours. The resulting powder is filtered, washed thrice with water and once with ethanol and dried at 110° C. Subsequently, the matrix is removed by heating the sample to 550° C. at 2° C./min. and held at this temperature for 12 hours.

The resulting white powdery product is suspended in a solution of NH$_3$ and CH$_3$COONH$_4$ (1:1 molar ratio) at 70° C. for 2 hours, filtered, washed, dried at 110° C. and calcined for 4 hours at 550° C. Properties of the resulting product are depicted in Table 1.

X-ray powder diffraction (XRPD) patterns obtained from the calcined sample shows the presence of only crystalline MFI-type material, i.e. ZSM-5. The pore size distributions obtained from the nitrogen isotherms measured at 77K reveals a bimodal pore size distribution with micropores of ~0.5 nm radius and mesopores in the range of 5–25 nm radius. The pore volumes of the micropores and mesopores were 0.09 and 0.5 mL/g, respectively. To demonstrate that the zeolite crystals are actually single crystals rather than just agglomerates of smaller crystals, selected area electron diffraction patterns were obtained from a number of crystals and they all showed single crystal properties. Inspection of high-resolution transmission electron micrographs from these single crystals also revealed that the lattice fringes extend through the entire crystal.

TABLE 1

| Property | Technique | Result |
| --- | --- | --- |
| Crystallinity | X-ray powder diffraction | Crystalline, MFI structure |
| Single crystal | TEM | Single crystal |
| Crystal size | SEM | 2 μm |
| Acidity as Si/Al molar ratio | Ammonia desorption | 116 |
|  | $^{27}$Al-NMR | 120 |
|  | Infrared spectroscopy[1] | 110 |
| Pore size | N$_2$ ads./des. At 77K, t-plot method | Micropores: ~0.5 nm radius |
|  | N$_2$ ads./des. At 77K, BJH method | Mesopores: 5–50 nm radius |
| Pore volume | N$_2$ ads./des. At 77K, t-plot method | Micropores: 0.09 mL/g |
|  | N$_2$ ads./des. At 77K, BJH method | Mesopores: 0.50 mL/g |

[1]Probe molecule was pyridine

Example 2

Preparation of Non-Mesoporous ZSM-5.

This sample was prepared to serve as a reference material 0.83 g of NaAlO$_2$ (54 w % Al$_2$O$_3$, 41 wt % Na$_2$O) is dissolved in a mixture of 80.0 g of tetrapropylammoniumhydroxide solution (TPAOH, 40 wt % aqueous solution) and 240 g of distilled water. 21.0 g a 40 wt % aqueous solution of colloidal silica (Ludox AS40, 40 wt % SiO$_2$ in water) is added under stirring. The resulting gel is hydrothermally treated in an autoclave. The autoclave is heated to 180° C. and held at this temperature for 48 hours. The resulting white powder is filtered, washed twice with water and once with ethanol, dried and calcined at 600° C. for 3 hours. The resulting white powdery product is suspended in a solution of NH$_3$ and CH$_3$COONH$_4$ (1:1 molar ratio) at 70° C. for 2 hours, filtered, washed, dried and calcined for 3 hours at 600° C. Properties of the resulting product are depicted in Table 2.

TABLE 2

| Property | Technique | Result |
| --- | --- | --- |
| Crystallinity | X-ray powder diffraction | 100% crystalline MFI-structure |

TABLE 2-continued

| Property | Technique | Result |
|---|---|---|
| Crystal size | Scanning electron microscopy | 2 μm |
| Acidity as Si/Al molar ratio | Ammonia desorption | 71 |
| | $^{27}$Al-NMR | 70 |
| | Infrared spectroscopy[2] | 70 |
| Pore size | N$_2$ ads./des. At 77K, t-plot method | Micropores: ~0.5 nm radius |
| | N$_2$ ads./des. At 77K, BJH method | Mesopores: n.a. |
| Pore volume | N$_2$ ads./des. At 77K, t-plot method | Micropores: 0.09 mL/g |
| | N$_2$ ads./des. At 77K, BJH method | Mesopores: n.a. mL/g |

[2]Probe molecule was pyridine

From the X-ray powder diffraction patterns obtained it is seen that the sample contains only ZSM-5. The pore size distributions obtained from the isotherms measured reveals a pore size distribution with micropores of ~0.5 nm radius. The pore volumes of the micropores were 0.09 mL/g.

Example 3

Preparation of Mesoporous 2.8 wt % Re/HZSM-5.

Rhenium (Re) is deposited by impregnation on the mesoporous ZSM-5 prepared according to Example 1 and as follows:

The mesoporous zeolite is dried at 120° C. for 2 hours and cooled to 25° C. in a desiccator. Then 0.1045 g NH$_4$ReO$_4$ dissolved in 4.2 g water is impregnated onto 2.5 g of the dried mesoporous zeolite. The impregnated zeolite is subsequently dried at 120° C. for 4 hours. The catalyst is tabletized, crushed and sieved to obtain a particle size of 212–355 μm. Before the catalytic test, 400 mg of the catalyst is mixed with 400 mg of quartz with a particle size of 200–300 μm. The mixture is inserted into a tubular fixed bed reactor of quartz with an inner diameter of 3.7 mm using quartz wool plugs to fix the catalyst bed. The catalyst is activated by heating to 300° C. in 1.5 hours and held at 300° C. for 1 hour, heated to 450° C. in 1 hour and held at this temperature for 2 hours all in flowing H$_2$ (12 Nml/h).

Example 4

Preparation of Non-Mesoporous 2.8 wt % Re/HZSM-5.

Rhenium (Re) is deposited on the non-mesoporous sample of ZSM-5 prepared according to Example 2 by impregnation. The procedure used in Example 3 was then followed.

Example 5

Preparation of Mesoporous Zn/HZSM-5.

Zinc is added to the mesoporous ZSM-5 by cation exchange with an aqueous 6 mol/L solution of Zn(NO$_3$)$_2$.6H$_2$O. 2.5 g of the mesoporous zeolite is added to 25 ml of the aqueous solution of Zn(NO$_3$)$_2$.6H$_2$O and the slurry is stirred at 85° C. for 5 hours with reflux. After the first ion exchange the slurry is filtered, the zeolite is washed with 200 ml of destilled water and is subsequently dried at 60° C. This procedure with ion exchange, filtering, washing and drying is repeated three times. The catalyst is tabletized, crushed and sieved to obtain a particle size of 212–355 μm. Before the catalytic test, 200 mg of the catalyst is mixed with 200 mg of quartz with a particle size of 200–300 μm. The mixture is inserted into a tubular fixed bed reactor of quartz with an inner diameter of 3.7 mm using quartz wool plugs to fix the catalyst bed. Prior to testing the catalyst is activated. The catalyst is heated to 300° C. in 1.5 hours and held at this temperature for 1 hour all in flowing N$_2$ (12 Nml/h).

Example 6

Preparation of Non-Mesoporous Zn/HZSM-5.

Zinc is added to non-mesoporous ZSM-5 as prepared in Example 2 using the process for preparation of mesoporous Zn-HZSM-5 given in Example 5.

Example 7

Ethane Dehydrogenation with Mesoporous Re/HZSM-5.

The catalyst from Example 3, mesoporous Re/HZSM-5, was contacted with a flow of ethane in a tubular fixed bed quartz reactor at a rate corresponding to a weight hourly space velocity (WHSV) of 2.3 at 550° C. and 1 atm. The effluent gasses were analysed by a Gas Chromatograph (GC) with a Thermal Conductivity Detector (TCD) and a Flame Ionisation Detector (FID). The GC was an HP6890A with a PONA column. Piping and valves were traced to 200° C. to avoid condensation of aromatics in the piping after the reactor or inside the GC. The results are shown in Table 3.

TABLE 3

| Mesoporous 2.8 wt % Re/HZSM-5 550° C., 1 atm., WHSV = 2.3 | TOS* = 0 h | TOS = 5 h | TOS = 10 h | TOS = 15 h | TOS = 20 h |
|---|---|---|---|---|---|
| Ethane conversion (mol %) | 14 | 13 | 13 | 13 | 13 |
| Ethylene selectivity (%) | 95 | 99 | 99 | 99 | 99 |
| Ethylene yield (mol %) | 13 | 13 | 13 | 13 | 13 |

*TOS = Time on stream, i.e. the time the catalyst has been contacted with the reactants stream at process conditions.

Example 8

Ethane Dehydrogenation with Non-Mesoporous Re/HZSM-5.

The catalyst from Example 4, non-mesoporous Re/HZSM-5, was contacted with a flow of ethane using the procedure described in Example 7. The results are shown in Table 4.

TABLE 4

| 2.8 wt % Re/HZSM-5 550° C., 1 atm., WHSV = 2.3 | TOS = 0 h | TOS = 5 h | TOS = 10 h | TOS = 15 h | TOS = 20 h |
|---|---|---|---|---|---|
| Ethane conversion (mol %) | 30 | 27 | 24 | 22 | 20 |
| Ethylene selectivity (%) | 18 | 21 | 31 | 49 | 65 |
| Ethylene yield (mol %) | 5 | 6 | 7 | 11 | 13 |

Example 9

Ethane Dehydrogenation with Mesoporous Zn/HZSM-5.

The catalyst from Example 5, mesoporous Zn/HZSM-5, was contacted with a flow of ethane using the procedure described in Example 7. The results are given in Table 5.

TABLE 5

| Mesoporous Zn/HZSM-5 550° C., 1 atm., WHSV = 2.3 | TOS = 0 h | TOS = 5 h | TOS = 10 h | TOS = 15 h | TOS = 20 h |
|---|---|---|---|---|---|
| Ethane conversion (mol %) | 11 | 12 | 12 | 13 | 14 |
| Ethylene selectivity (%) | 99 | 85 | 80 | 79 | 79 |
| Ethylene yield (mol %) | 11 | 10 | 10 | 10 | 11 |

Example 10

Ethane Dehydrogenation with Non-Mesoporous Zn/HZSM-5.

The catalyst from Example 6, non-mesoporous Zn/HZSM-5, was contacted with a flow of ethane in a tubular fixed bed quartz reactor at a rate corresponding to a WHSV of 1.8 at 550° C. Otherwise the procedure of Example 7 was followed. The results are given in Table 6.

TABLE 6

| Zn/HZSM-5 550° C., 1 atm., WHSV = 1.8 | TOS = 0 h | TOS = 5 h | TOS = 10 h | TOS = 15 h | TOS = 20 h |
|---|---|---|---|---|---|
| Ethane conversion (mol %) | 50 | 36 | 28 | 22 | 17 |
| Ethylene selectivity (%) | 4 | 8 | 14 | 36 | 61 |
| Ethylene yield (mol %) | 2 | 3 | 4 | 8 | 10 |

Example 11

Propane Dehydrogenation with Mesoporous Re/HZSM-5.

The catalyst from Example 3, mesoporous Re/HZSM-5, was contacted with a flow of propane in a tubular fixed bed quartz reactor at a rate corresponding to a WHSV of 2.3 at 550° C. following the procedure of Example 7. The results are given in Table 7.

TABLE 7

| Mesoporous 2.8 wt % Re/HZSM-5 550° C., 1 atm., WHSV = 2.3 | TOS = 0 h | TOS = 10 h |
|---|---|---|
| Propane conversion (mol %) | 41.7 | 25.1 |
| Propylene selectivity (%) | 58.2 | 73.9 |
| Propylene yield (mol %) | 24.2 | 18.6 |

Example 12

Propane Dehydrogenation with Non-Mesoporous Re/HZSM-5.

The catalyst from Example 4, non-mesoporous Re/HZSM-5, was contacted with a flow of propane using the procedure described in Example 7. The results are shown in Table 8.

TABLE 8

| 2.8 wt % Re/HZSM-5 550° C., 1 atm., WHSV = 2.3 | TOS = 0 h | TOS = 10 h |
|---|---|---|
| Propane conversion (mol %) | 74.6 | 30.9 |
| Propylene selectivity (%) | 8.1 | 57.8 |
| Propylene yield (mol %) | 6.1 | 17.8 |

As mentioned earlier, formation of carbonaceous species, i.e. coke, is an inherent problem in catalytic dehydrogenation processes, which affects the process economy by lowering the yield of desired products as well as lowering the activity of the catalyst. A catalyst with increased selectivity towards the primary products, i.e. the corresponding olefins, is therefore highly desirable.

The results obtained from catalysts based on mesoporous ZSM-5 compared with non-mesoporous ZSM-5 in the Examples 7 to 12 demonstrate the increased selectivity towards olefins. They also demonstrate the significantly lowered or absent deactivation rates of the catalysts based on mesoporous ZSM-5 (Examples 7, 9 and 11) compared to the catalysts based on non-mesoporous ZSM-5 (Examples 8, 10 and 12).

A study of the results obtained in the examples above with respect to conversion of ethane with the various catalysts revealed that mesoporous 2.8 wt % Re/HZSM-5 and mesoporous Zn/HZSM-5 both show relatively constant conversions of ethane of 13% and 12%, respectively. The deactivation is almost non-existent and the conversion of ethane on the mesoporous Zn/HZSM-5 is apparently increasing.

In contrast to this, the zinc ion exchanged non-mesoporous zeolite is strongly deactivated over a period of 24 hours, while the rhenium impregnated non-mesoporous ZSM-5 is less deactivated. Nevertheless, it is faster deactivated than the mesoporous zeolites. Though the initial conversions over the non-mesoporous 2.8 wt % Re/HZSM-5 and Zn/HZSM-5 are approximately 50% and 30%, respectively, the conversions after a period of 24 hours are of the same magnitude as for the mesoporous zeolites.

A study of the selectivity and yield for ethylene with the various catalysts obtained in the results above shows that the ethylene selectivity on the mesoporous 2.8 wt % Re/HZSM-5 is very high and relatively constant not less than 95 wt % and converging to 100 wt %. Apart from ethylene, the rest of the products include only hydrocarbon compounds with three carbon atoms.

The mesoporous Zn/HZSM-5 has a high initial selectivity, which after 10 hours falls to a relatively constant value of approximately 78%. The rest of the products include C3 hydrocarbon compounds, benzene and toluene.

The non-mesoporous 2.8 wt % Re/HZSM-5 has an initial ethylene selectivity of 18%, which increases to 76% after 24 hours. With the exception of ethylene, it was observed that hydrocarbons with three and four carbon atoms, benzene, toluene, xylene and styrene were detected as products from the conversion of ethane.

The ethylene selectivity on non-mesoporous Zn/HZSM-5 is initially 4%, but increases to 77% after 24 hours. Both C3, C4, benzene, toluene, xylene, styrene, trimethylbenzene, naphtalene, methylnaphtalene and dimethylnaphtalene are detected in the products.

The invention claimed is:

1. A process for catalytic dehydrogenation of a dehydrogenatable hydrocarbon process stream to the corresponding olefin or olefins, the process comprising contacting the dehydrogenation conditions with a mesoporous zeotype catalyst having an intra-crystalline, non-crystallographic mesopore system and a mesopore volume of the zeotype crystals above 0.25 ml/g and comprising at least one element belonging to Groups 5–14.

2. A process according to claim 1, wherein the at least one element is chosen from the group of chromium (Cr), Molybdenum (Mo), Wolfram (W), Rhenium (Re), Rhodium (Rh), Iridium, Nickel (Ni), Palladium (Pd), Platinum (Pt), Copper (Cu), Silver (Ag), Zinc (Zn), Gallium (Ga), Indium (In) and Tin (Sn).

3. A process according to claim 1, wherein the at least one element is Re.

4. A process according to claim 1, wherein the at least one element is Pt and Sn.

5. A process according to claim 1, wherein the at least one element is in the form of the metal, the carbide, the oxide or the nitride.

6. A process according to claim 1, wherein the zeotype is a mesoporous zeolite.

7. A process according to claim 6, wherein the mesoporous zeolite is mesoporous ZSM-5 or mesoporous HZSM-5.

8. A process according to claim 1, wherein the dehydrogenatable hydrocarbon process stream contains one or more dehydrogenatable compounds belonging to the group $R-CH_2-CH_3$, where $R=H$ or $C_{1-4}$.

9. A process according to claim 8, wherein the dehydrogenatable compound is ethane, propane, n-butane or i-butane.

10. A process according to claim 1, wherein the dehydrogenatable process stream contains a mono-cyclic aromatic compound.

11. A process according to claim 10, wherein the monocyclic aromatic compound is ethyl benzene or paraethyl methyl benzene.

12. A catalyst for use in a dehydrogenation process, wherein the catalyst comprises a mesoporous zeotype catalyst having an intra-crystalline, non-crystallographic mesopore system and a mesopore volume of the zeotype crystals above 0.25 ml/g and comprising at least one element selected from the group consisting of Chromium (Cr), Molybdenum (Mo), Wolfram (W), Rhenium (Re), Rhodium (Rh), Iridium (Ir), Nickel (Ni), Palladium (Pd), Platinum (Pt), Copper (Cu), Silver (Ag), Zinc (Zn), Gallium (Ga), Indium (In) and Tin (Sn).

* * * * *